(12) United States Patent
Blaine et al.

(10) Patent No.: US 10,677,003 B2
(45) Date of Patent: Jun. 9, 2020

(54) CAPTURE OF DRILLING FLUID RETURNS

(71) Applicant: MINEX CRC LTD, Kensington, Western Australia (AU)

(72) Inventors: Fred Blaine, Dulwich (AU); Andrew Beach, Balcatta (AU); James Barry Reilly, Bayswater (AU)

(73) Assignee: MINEX CRC LTD, Kensington, Western Australia (AU)

( * ) Notice: Subject to any disclaimer, the term of this patent is extended or adjusted under 35 U.S.C. 154(b) by 53 days.

(21) Appl. No.: 15/752,789

(22) PCT Filed: Aug. 12, 2016

(86) PCT No.: PCT/AU2016/000282
§ 371 (c)(1),
(2) Date: Feb. 14, 2018

(87) PCT Pub. No.: WO2017/027901
PCT Pub. Date: Feb. 23, 2017

(65) Prior Publication Data
US 2018/0230762 A1    Aug. 16, 2018

(30) Foreign Application Priority Data
Aug. 14, 2015  (AU) ................................. 2015903272

(51) Int. Cl.
*E21B 21/01*   (2006.01)
*E21B 21/06*   (2006.01)
(Continued)

(52) U.S. Cl.
CPC ............ *E21B 21/01* (2013.01); *E21B 21/065* (2013.01); *E21B 49/005* (2013.01); *G01N 33/2823* (2013.01); *E21B 2021/007* (2013.01)

(58) Field of Classification Search
CPC ...................................................... E21B 21/01
See application file for complete search history.

(56) References Cited

U.S. PATENT DOCUMENTS 4,149,603 A    4/1979   Arnold
5,121,796 A    6/1992   Wigington, Sr.
(Continued)

FOREIGN PATENT DOCUMENTS

AU    2012318265 A1    6/2013
AU    2013204746 A1    6/2013

OTHER PUBLICATIONS

International Search Report and Written Opinion of the ISA for PCT/AU2016/000282, ISA/AU, Woden ACT, dated Oct. 17, 2016.
(Continued)

*Primary Examiner* — David J Bagnell
*Assistant Examiner* — Brandon M Duck
(74) *Attorney, Agent, or Firm* — Stites & Harbison, PLLC; Terry L. Wright (57) ABSTRACT

An apparatus (10) for capturing drilling fluid returns in an exploration drilling process, as well as a related method of capturing the drilling fluid returns. The apparatus (10) is adapted to be fitted onto a drill collar/casing (11) adjacent its open top (13). The apparatus (10) comprises a body (21) defining a reservoir (23) for receiving the drilling fluid returns flowing out through the open top end (13) of the drill collar/casing (11) and spilling into the reservoir (23). The reservoir (23) comprises a collecting portion (25) in which the fluid returns spilling from the drill collar/casing (11) can be collected. The reservoir (23) also comprises a sump portion (27) which can receive the drilling fluid returns and from which the drilling fluid returns can be pumped by way of a sump pump (28). The reservoir (23) is configured to direct the drilling fluid returns collected by the collecting portion (25) to the sump portion (27) as a continuous flow.

10 Claims, 7 Drawing Sheets

(51) Int. Cl.
*G01N 33/28* (2006.01)
*E21B 49/00* (2006.01)
*E21B 21/00* (2006.01)

(56) References Cited

U.S. PATENT DOCUMENTS

| | | |
|---|---|---|
| 5,228,506 A | 7/1993 | Pearce |
| 5,377,748 A * | 1/1995 | Gayaut .................. E21B 21/01 166/162 |
| 5,634,485 A | 6/1997 | Holtby |
| 2006/0021796 A1 | 2/2006 | Moran |
| 2014/0262315 A1 | 9/2014 | Boisjolie et al. |

OTHER PUBLICATIONS

IP Australia, Examination Report No. 1 issued in corresponding Application No. 2018201126, dated Feb. 4, 2019.
European Patent Office, Extended European Search Report issued in corresponding Application No. 16836258, dated Mar. 7, 2019.

* cited by examiner

CAPTURE OF DRILLING FLUID RETURNS

CROSS-REFERENCE TO RELATED APPLICATIONS

This application is a 371 U.S. National Stage of International Application No. PCT/AU2016/000282, filed Aug. 12, 2016, which claims the benefit of and priority to Australian Patent Application No. 2015903272, filed Aug. 14, 2015. The disclosures of the above applications are incorporated herein by reference.

TECHNICAL FIELD

The present invention relates to capture of drilling fluid returns in an exploration drilling process. The captured drilling fluid returns may be used in sampling systems and methods in exploration drilling.

BACKGROUND ART

The following discussion of the background art is intended to facilitate an understanding of the present invention only. The discussion is not an acknowledgement or admission that any of the material referred to is or was part of the common general knowledge as at the priority date of the application.

In exploration drilling such as mineral exploration drilling, there is a need obtain representative samples for analysis to determine the geology of the earth formation being drilled.

The current practice when performing exploration drilling, such as mineral exploration drilling, is to send samples obtained during the course of drilling (e.g. core samples obtained from diamond drilling) to a laboratory (which is usually located remotely from the drilling site) for analysis to determine the geology of the earth formation that is being drilled. This usually results in a significant delay between the time that the samples are obtained and the time that the results of the analysis of the samples by the laboratory become available. The delay can be in the order of weeks or months. The delay in obtaining the analysis means that there is minimal, if any, feedback available for use in making decisions while drilling.

In an effort to reduce the aforementioned delay, there have been proposals to use drilling cuttings as a source of analysis to determine the geology of the earth formation that is being drilled. In this way, the drilling cuttings would constitute a continuous stream of sample material representative of the geological formation being drilled.

Typically in a drilling process, the drilling cuttings are conveyed to ground surface in a fluid, such as a drilling fluid (commonly referred to a drilling mud). The fluid can be captured and conveyed to a separation system at which at least some of the cuttings are removed. The removed cuttings can then be used for sampling. In one arrangement, all of the removed cuttings might be used for sampling; either as a continuous sample for analysis, or by being separated into batches providing individual samples for analysis. In another arrangement, only a portion of the removed cuttings are used for sampling; either as a continuous sample for analysis, or by being separated into batches providing individual samples for analysis.

The drilling fluid may form part of a fluid system, in which the drilling fluid is pumped down the drill string and returns upwardly along an annular space about the drill string, carrying the drilling cuttings. The returning fluid with the entrained drilling cuttings, is referred to herein as the drilling fluid returns.

The drilling fluid returns are captured in any appropriate way; for example, by collection at the upper end of a drill casing which extends into the borehole and along which the drill string passes, with the annular space around the drill string being defined between the drill string and the surrounding portion of the casing.

The fluid system may have a separation system at which at least some of the cuttings are removed from the drilling fluid returns. The separation system may separate the drilling cuttings in any appropriate way. The separation system may, for example, comprise a fluid flow path along which the drilling fluid returns can be conveyed, the fluid flow path incorporating a centrifuge for removal of cutting solids from the drilling fluid. The separation system may comprise part of a solids control system forming part of the fluid system. A solids control system likely to be particularly suitable is of the type disclosed in Australian Patent Applications 2012318265 and 2013204746, the contents of which are incorporated herein by way of reference.

There is need also to relate each sample to the axial location within the borehole at which the particular sample has been collected.

The samples may be taken incrementally by sampling in time intervals which represent specific spatial intervals of the borehole. By way of example, one or more samples may be taken at specific times, each specific time being related to the location within the borehole at which the drilling cuttings (providing the sample or samples) have been taken. In this manner, each sample is related generally to the location within the borehole at which the particular sample has been collected. The incremental samples can in collected and stored individually for subsequent analysis; for example, in sample collection bags.

In capturing the drilling fluid returns, it is desirable to collect the drilling fluid returns and convey the collected drilling fluid returns a continuous flow stream to a subsequent stage (at which drilling cuttings are to be removed from the drilling fluid). Collecting the drilling fluid returns and conveying the collected drilling fluid returns as a continuous flow stream serves to maintain the drilling cuttings in suspension within the drilling fluid. Maintaining the drilling cuttings in suspension within the drilling fluid is advantageous, as it may assist in avoiding blending of drill cuttings from different axial locations in the borehole, which would likely arise in circumstances where there was settling of the drill cuttings prior to removal from the drilling fluid. Blending of drill cuttings from different axial locations in the borehole may lead to samples which are less representative of the particular axial locations of the borehole to which discrete samples are attributed.

It is against this background that the present invention has been developed.

While the present invention has been developed against this background, it need not necessarily overcome any or all of the problems and difficulties referred to above. Rather, the invention may merely offer an alternative arrangement for facilitating the capture of drilling fluid returns in an exploration drilling process.

SUMMARY OF INVENTION

According to a first aspect of the invention there is provided apparatus for capturing drilling fluid returns discharging from an outlet in an exploration drilling process, the apparatus comprising a body defining a reservoir for receiving the drilling fluid returns, the body being adapted for sealing engagement with the outlet whereby the reservoir is disposed to receive drilling fluid returns discharging from the outlet, the reservoir having a sump portion for receiving the drilling fluid returns and from which the drilling fluid returns can be pumped.

Typically, the outlet from which the drilling fluid returns discharge during the exploration drilling process would comprise a drill collar or casing which is installed in a borehole being drilled and into which a drill string can be received for performing the drilling operation, the drill collar/casing having a top end surrounding the point of entry of the drill string into the casing.

The reservoir may have an open top through which the drilling fluid returns can flow into the reservoir. Typically, the drilling fluid returns would flow from the top end of the drill collar/casing, spilling down into the reservoir through the open top.

The reservoir may be configured to direct the captured drilling fluid returns towards the sump portion.

The reservoir may have a sloping bottom portion for directing the drilling fluid returns towards the sump portion.

The reservoir may be configured to direct the captured drilling fluid returns received by the sump portion to an outlet from the sump portion.

The reservoir may have a further sloping bottom portion for directing the drilling fluid returns received by the sump portion to the outlet from the sump portion.

The outlet from the sump portion may comprise an intake of a pump in fluid communication with the sump portion.

The sump portion may be incorporated into the confines of the reservoir.

In one arrangement the reservoir comprises a bottom, the bottom comprising the two sloping bottom portions.

The reservoir may further comprise a collecting portion, the collecting portion being arranged to receive the drilling fluid returns, the arrangement being that the drilling fluid returns entering the collecting portion can continuously flow to the sump portion, from where the drilling fluid returns can flow continuously to the outlet from the sump portion.

The collecting portion and the sump portion may be in contiguous relation within the reservoir, blending together within the interior of the reservoir.

The reservoir may also comprise a side wall upstanding from the bottom.

The side wall may be configured to define the collecting portion and the sump portion.

The side wall may comprise two straight wall sections in generally opposed relation and two curved wall sections at opposed ends of the straight wall sections, with the collecting portion being defined by the two straight wall sections and one curved wall section, and the sump portion being defined by the other curved wall section.

The two straight wall sections may be disposed angularly with respect to each other, whereby the spacing between the straight wall sections is larger at one of the said opposed ends and the other, and said one curved wall section being at the larger of the opposed ends.

The body may be adapted to be fitted around the outlet, with the collecting portion surrounding the outlet.

The body may have provision for the casing to extend through the reservoir, thereby permitting the body to be fitted around the outlet.

The body may have an opening for receiving the casing, with the casing extending through the reservoir.

A seal means may be provided for said sealing engagement with the outlet. The seal means may provide sealing engagement between the body and the outlet, whereby drilling fluid returns discharging from the outlet can flow into the reservoir.

The seal means may be adapted to accommodate one outlet size or a plurality of outlet sizes.

The seal means may comprise a sealing collar adapted to be fitted around the drill collar/casing in sealing engagement therewith.

The sealing collar may be provided within the reservoir in sealing engagement with the bottom.

The sealing collar may comprise a resilient seal.

The resilient seal may be of frusto-conical configuration, having a smaller end section configured for sealing engagement with the drill collar/casing and a larger end section in sealing engagement with the body.

In one arrangement, the apparatus may further comprise a pump for pumping captured fluid returns from the sump portion. In another arrangement, the apparatus may have provision for establishing fluid communication between the sump portion and a pump. Where the apparatus comprises a pump, the latter may comprise an integrated sump pump. Where the apparatus has provision for establishing fluid communication between the sump portion and a pump, said provision may comprise means to mount a sump pump on the body in fluid communication between the sump portion.

According to a second aspect of the invention there is provided a method of capturing drilling fluid returns comprising use of apparatus according to the first aspect of the invention.

According to a third aspect of the invention there is provided a method of capturing drilling fluid returns discharging from an outlet, the method comprising positioning a reservoir about the outlet, receiving drilling fluid returns discharging from the outlet in the reservoir, conveying the received drilling fluid returns as a continuous flow to a sump, and pumping drilling fluid returns from the sump.

BRIEF DESCRIPTION OF THE DRAWINGS

Further features of the present invention are more fully described in the following description of a non-limiting embodiment thereof. This description is included solely for the purposes of exemplifying the present invention. It should not be understood as a restriction on the broad summary, disclosure or description of the invention as set out above. The description will be made with reference to the accompanying drawings in which.

In the drawings like structures are referred to by like numerals throughout the several views. The drawings shown are not necessarily to scale, with emphasis instead generally being placed upon illustrating the principles of the present invention.

The figures which constitute the drawings depict an exemplary embodiment of the invention. The embodiment illustrates certain configurations; however, it is to be appreciated that the invention can take the form of many configurations, as would be obvious to a person skilled in the art, whilst still embodying the present invention. These configurations are to be considered within the scope of this invention.

DESCRIPTION OF EMBODIMENT

Referring to the drawings, there is shown apparatus 10 for capturing returning drilling fluids which have been cycled through a borehole (not shown) being sampled during the drilling process. The drilling process may, for example, comprise exploration drilling, such as mineral exploration drilling by way of diamond drilling.

In a drilling process, the drilling cuttings are conveyed to ground surface in the returning drilling fluid (the drilling fluid returns). The drilling fluid returns are captured apparatus 10 and conveyed to a separation system at which at least some of the drilling cuttings (drilling solids) are removed for sampling.

The apparatus 10 maintains the drilling cuttings, which comprise particulate material generated through drilling, in suspension within the drilling fluid and directs the captured drilling fluid returns to a separation system. The separation system may comprise a solids control system forming part of the drilling fluid system (commonly known as a mud system) used in conjunction with the drilling process. A solids control system likely to be particularly suitable is of the type disclosed in Australian Patent Applications 2012318265 and 2013204746, the contents of which are incorporated herein by way of reference.

In the drilling process, a casing is provided in the borehole and a drill collar attached to the casing. A drill string is inserted into the casing to perform the drilling operation, as is well understood by persons skilled in the art. In the arrangement shown, the drill collar/casing is depicted in some of the drawings to facilitate further description of the apparatus 10, and is identified by reference numeral 11.

In drilling process, drilling fluid is pumped down the drill string and returns upwardly along an annular space between the drill string and the casing, carrying the drilling cuttings. The returning fluid with the entrained drilling cuttings is referred to herein as the drilling fluid returns, as previously mentioned. The drill collar/casing 11 thus provides an outlet for the drilling fluid returns.

The apparatus 10 is fitted onto the drill collar/casing 11 adjacent the open top 13 thereof, as will be explained in more detail later, to capture all of the drilling fluid returns flowing out through the open top end 13 and spilling into the apparatus 10.

The apparatus 10 is adapted to be fitted onto the drill collar/casing 11, below but in close proximity to the top end 13. The apparatus 10 can assume a variety of angular positions around the drill collar/casing 11, according to requirements and the availability of space at the location concerned.

The apparatus 10 comprises a body 21 defining a reservoir 23 for receiving the drilling fluid returns, the body 21 being adapted for sealing engagement with the drill collar/casing 11 whereby drilling fluid returns discharging from the borehole can flow into the reservoir.

Figure 4:
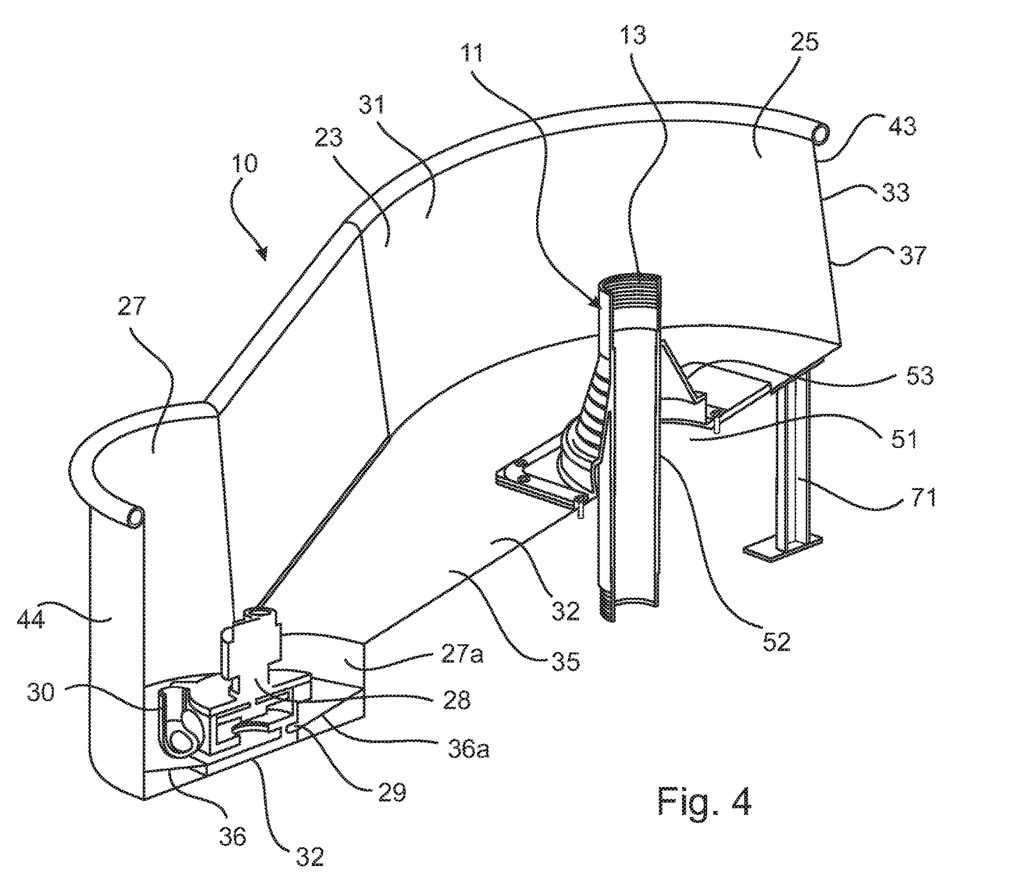
FIG. 4 is a sectional perspective view of the apparatus.
Figure 5:
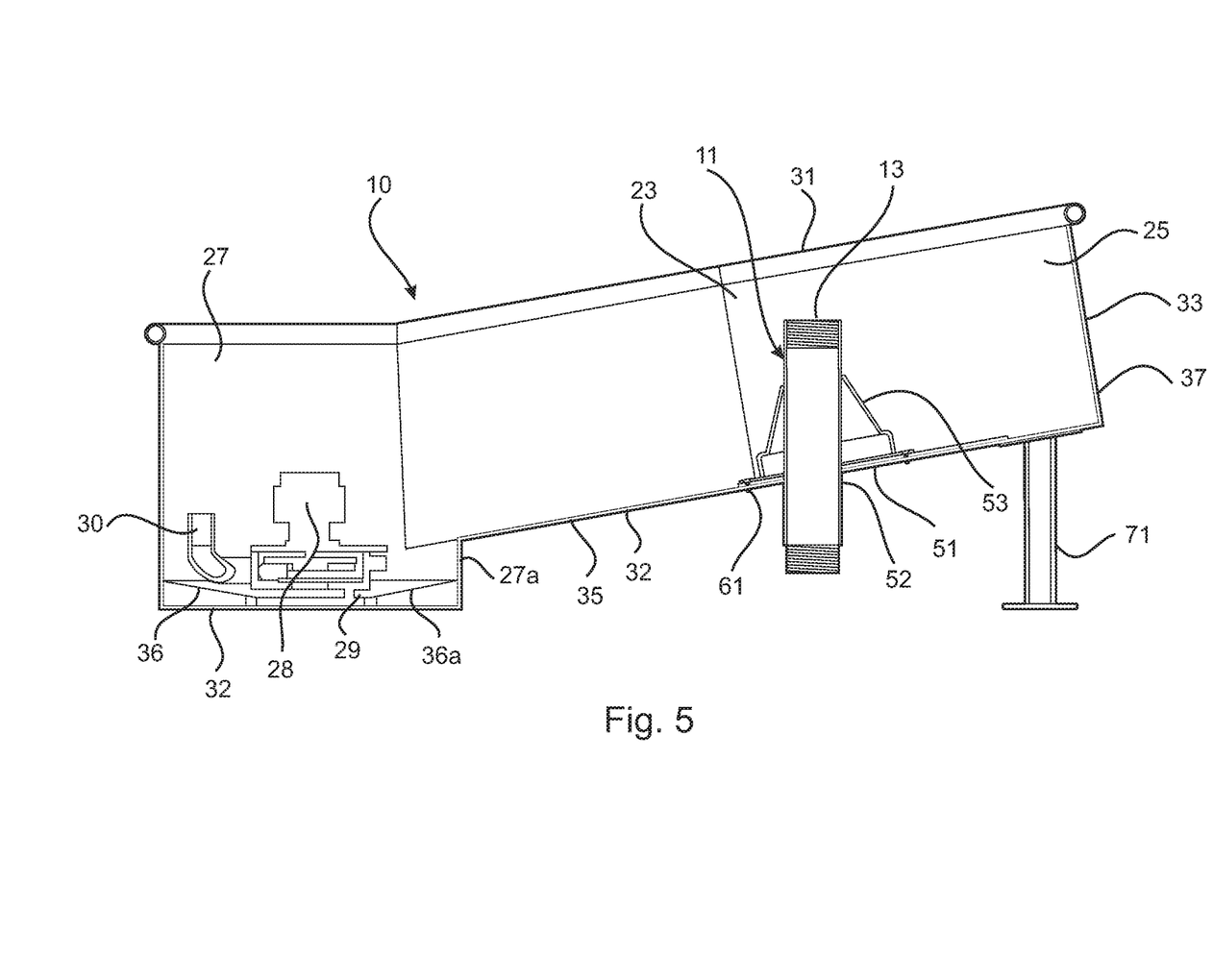
FIG. 5 is a sectional side view of the apparatus.

The reservoir 23 comprises a collecting portion 25 in which the fluid returns spilling from the drill collar/casing 11 can be collected, and a sump portion 27 for receiving the drilling fluid returns and from which the drilling fluid returns can be pumped by way of an integrated sump pump 28 (as shown in FIGS. 4 and 5). The sump pump 28 has intake port(s) 29. In the arrangement shown, the sump portion 27 includes a recessed portion at the bottom section thereof which provides a sump 27a in which the sump pump 28 is accommodated. The arrangement is such that the drilling fluid returns spilling from the drill collar/casing 13 can continuously enter the collecting portion 25 of the reservoir 23 and flow continuously to the sump portion 27, from where the drilling fluid returns can flow continuously into the sump 27a for communication with the intake port(s) 29 of the sump pump 28. The sump pump 28 has a discharge outlet 30 to which a fluid line (not shown) can be connected for delivery of the captured drilling fluid returns to a separation system at which at least some of the drilling cuttings are removed for sampling. With this arrangement, the sump pump 28 provides an outlet from the sump portion 27.

The collecting portion 25 and the sump portion 27 are in contiguous relation within the reservoir 23, blending together within the interior 24 of the reservoir.

The reservoir 23 has an open top 31 through which the drilling fluid returns can flow into the collecting portion 25. The drilling fluid returns flow from the top end 13 of the drill collar/casing 11, spilling down into the collecting portion 25 through the open top 31 of the reservoir 23.

The reservoir 23 is configured to direct the captured drilling fluid returns collected by the collecting portion 25 to the sump portion 27. For this purpose, the collecting portion is disposed angularly with respect to the sump portion 27, as best seem in FIG. 3.

The reservoir 23 defined by the body 21 has a bottom 32 and a side 33. The bottom 32 comprises a sloping bottom portion 35 within the collecting portion 25 for directing the collected drilling fluid returns towards the sump portion 27. The sump portion 27 comprises a sloping bottom portion 36 within the sump 27a for directing the drilling fluid returns received in the sump portion 27 to the intake port(s) 29 of the sump pump 28. The intake port(s) 29 of the sump pump 28 are positioned at the level of, or closely adjacent, the sloping bottom portion 36 within the sump portion 27. In the arrangement shown, the sloping bottom portion 36 comprises a "false" bottom 36a above the bottom 32 of the body 21.

The side 33 comprises a side wall 37 upstanding from the bottom 32.

The side wall 37 is configured to define the collecting portion 25 and the sump portion 27. In the arrangement shown, the side wall 37 comprises two straight wall sections 41, 42 in generally opposed relation and two curved wall sections 43, 44 at opposed ends of the straight wall sections. The collecting portion 25 is defined by the two straight wall sections 41, 42 and first curved wall section 43. The sump portion 27 is defined by second curved wall section 44. The two straight wall sections 41, 42 are disposed angularly with respect to each other, whereby the spacing between the straight wall sections 41, 42 is larger at one of the said opposed ends and the other. The first curved wall 43 is at the larger of the opposed ends, and the second curved wall section 44 is at the smaller of the opposed ends.

The body 21 adapted to be fitted around the drill collar/casing 11 with the collecting portion 25 surrounding the drill collar/casing, as shown in the drawings, to capture drilling fluid returns spilling from the open top end 13.

The body 21 has an opening 51 for receiving the drill collar/casing 11, with the drill collar/casing extending through the reservoir 23. The opening 51 comprises a hole 52 in the bottom 32.

A seal means 53 may be provided for sealing engagement with the side of the drill collar/casing 13. The seal means 53 functions to provide sealing engagement between the body 21 and the drill collar/casing 11, whereby drilling fluid returns discharging from the top end 13 can flow into the reservoir 23.

The seal means 53 is adapted to accommodate a variety of sizes in which the drill collar/casing 11 may come.

The seal means 53 comprise a sealing collar 55 adapted to be fitted around the drill collar/casing 11 in sealing engagement therewith.

The sealing collar 55 provided within the reservoir 23 in sealing engagement with the bottom 32 in the region surrounding the hole 52.

Figure 6:
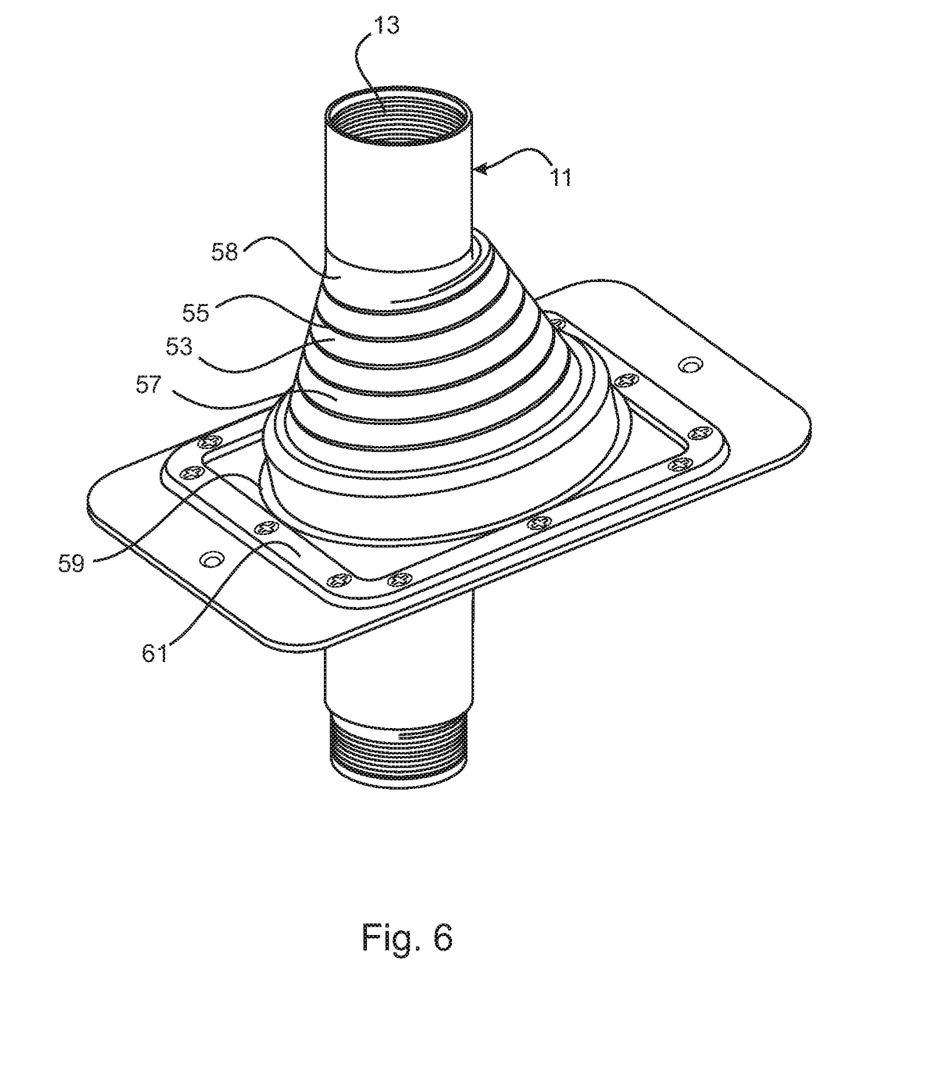
FIG. 6 is a fragmentary perspective view illustrating a seal forming part of the apparatus, the seal being depicted in engagement with a drill collar/casing used in a drilling system with which the apparatus is used.
Figure 7:
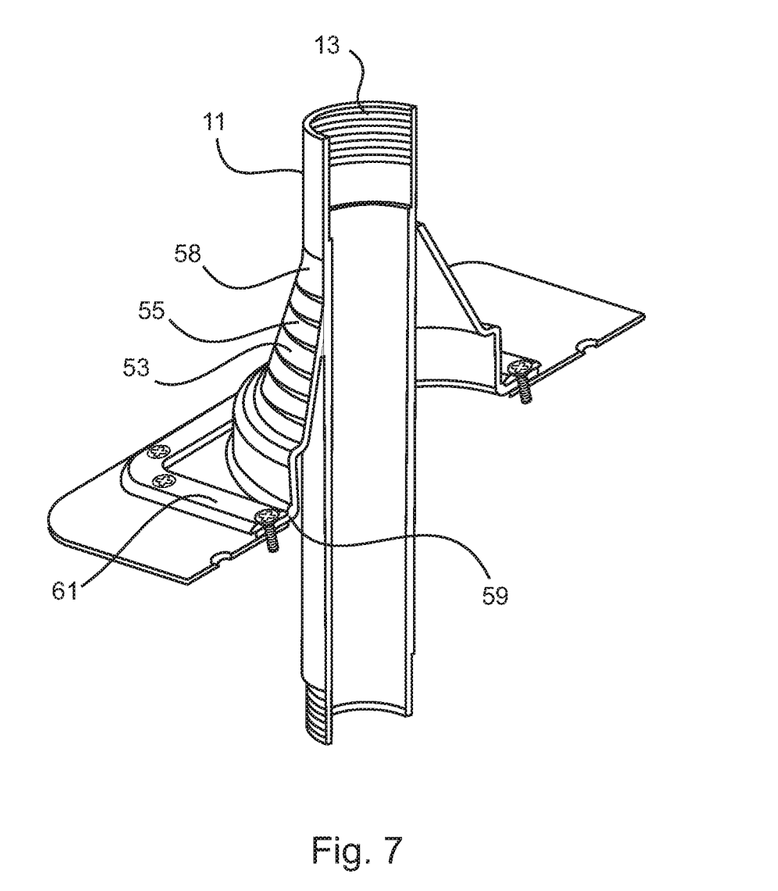
FIG. 7 is a view similar to FIG. 6 except that it is a sectional view.

The sealing collar 55 comprises a resilient seal 57. In the arrangement shown, the resilient seal 57 is of frusto-conical configuration, having a smaller end section 58 configured for sealing engagement with the drill collar/casing 11 and a larger end section 59 in sealing engagement with the body 21 at the bottom 32 in the region surrounding the hole 52. The larger end section 59 of the resilient seal 57 is secured in sealing engagement with the bottom 32 by way of a mounting plate assembly 61. More particularly, the mounting plate assembly 61 is attached between the larger end section 59 of the frusto-conical resilient seal 57 and the bottom 32 of the reservoir 23, to secure the frusto-conical resilient seal 57 in sealing engagement with the body 21, as best seen in FIGS. 4 and 5. The mounting plate assembly 61 is shown in FIGS. 6 and 7 secured the larger end section 59 of the frusto-conical resilient seal 57 but not attached to the bottom 32 of the reservoir 23.

Within this arrangement, the body 21 is adapted to be fitted around the drill collar/casing 11, with the collecting portion 25 surrounding the drill collar/casing 11. The collecting portion 25, in effect, provides a moat around the sealing collar 55, which thereby also surrounds the drill collar/casing 11 to receive drilling fluid returns discharging from the top end 13.

Figure 1:
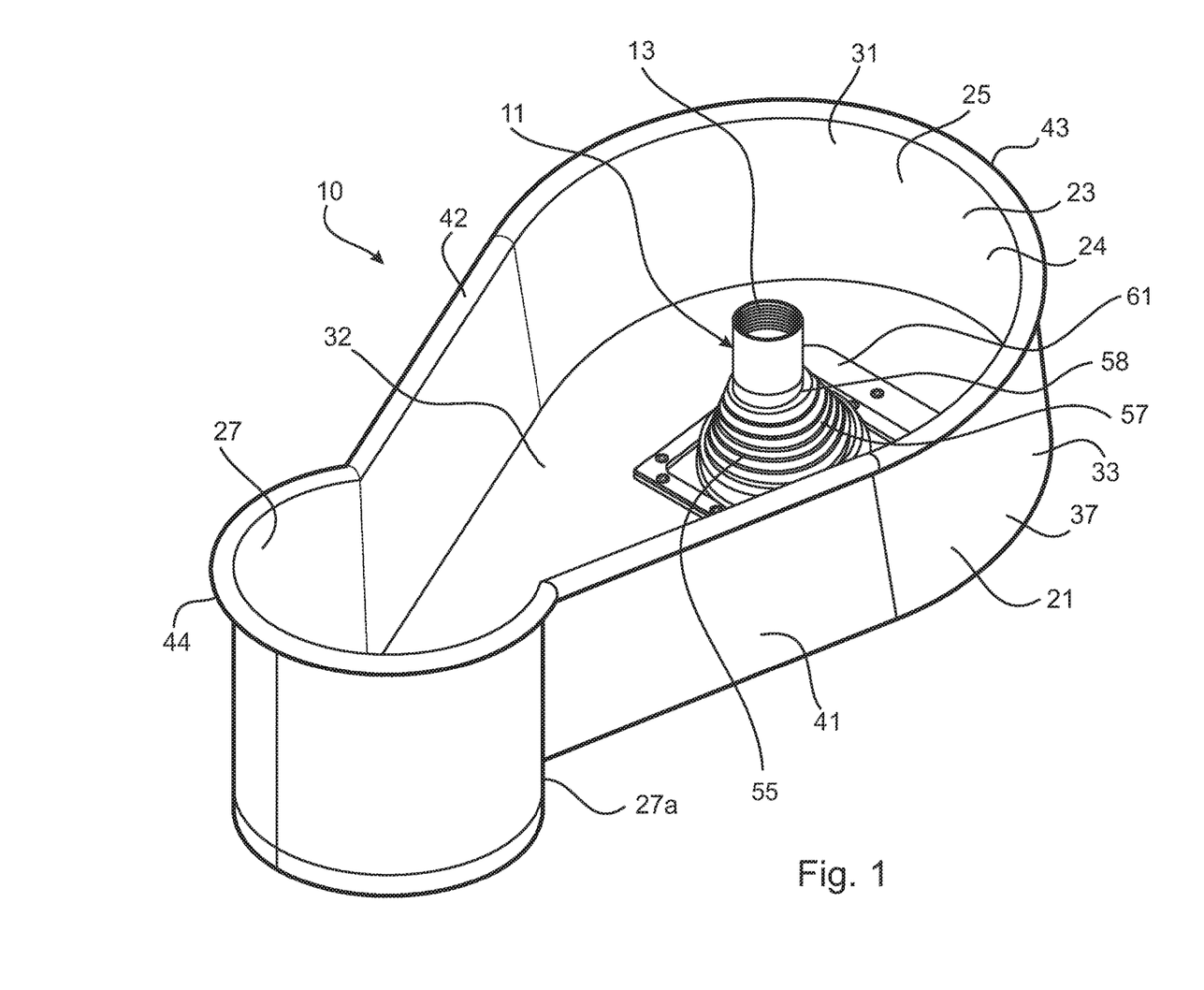
FIG. 1 is a perspective view from above of an embodiment of an apparatus for capturing drilling fluid returns.
Figure 2:
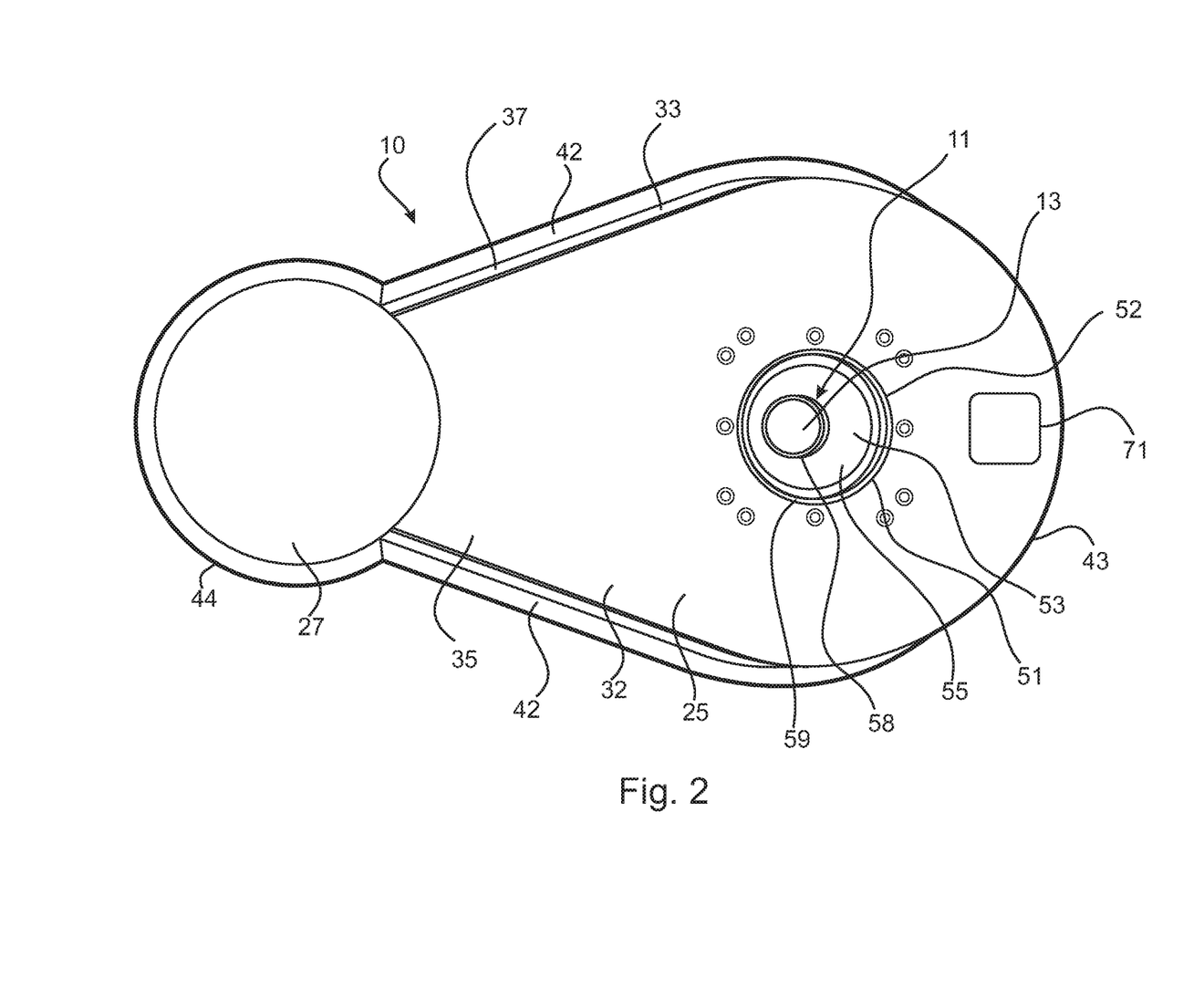
FIG. 2 is an underside view of the apparatus.
Figure 3:
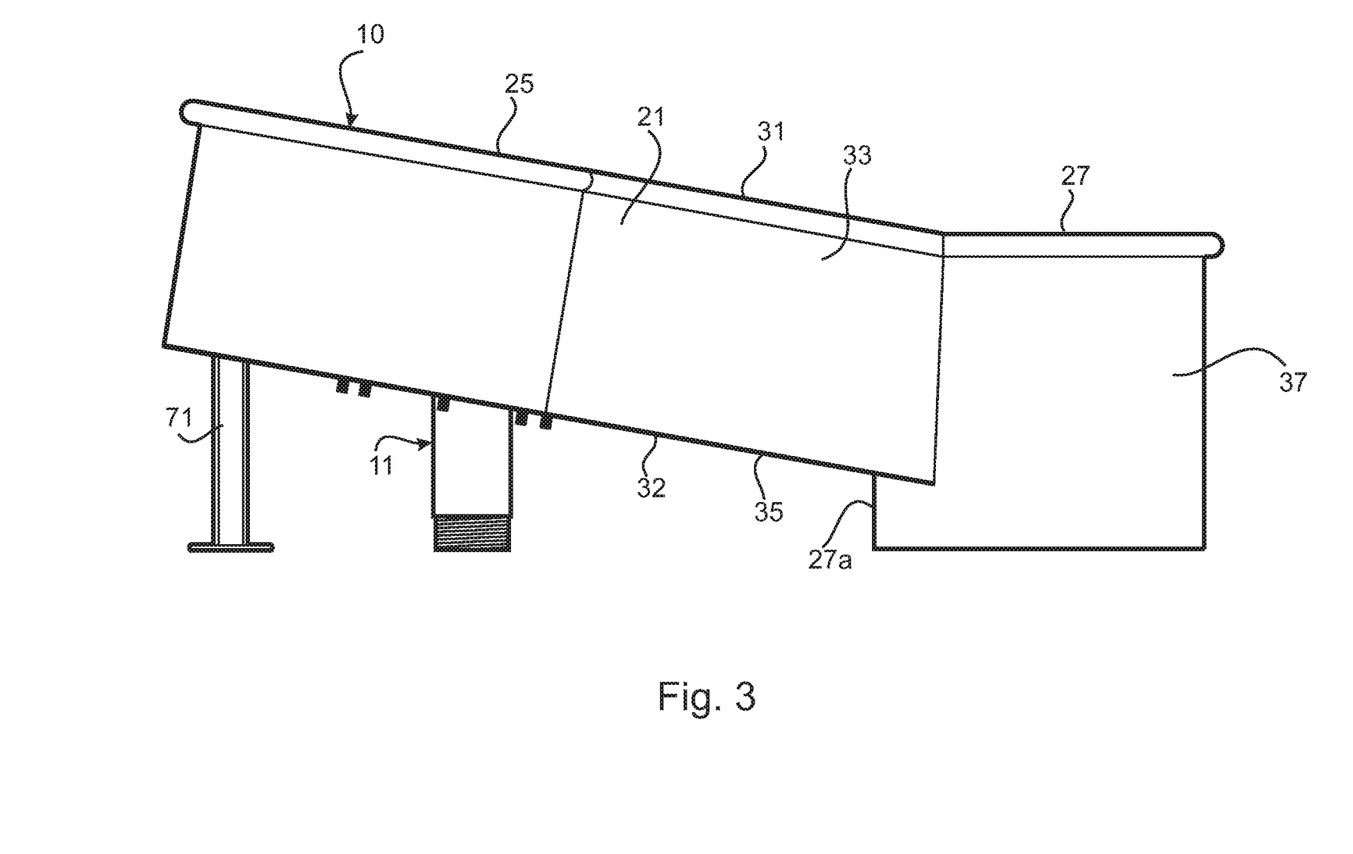
FIG. 3 is a side view of the apparatus.

The body 21 is fitted with a stand or other structure 71 to facilitate installation of the apparatus 10 in position about the drill collar/casing 11. The stand or other structure 71 also accommodates the angular disposition of the collecting portion 25 with respect to the sump portion 27, as best seen in FIGS. 3 and 5.

The arrangement permits the apparatus 10 to be positioned at a variety of angular positions around the drill collar/casing 11, according to requirements and the availability of space at the drilling location. It also facilitates mounting under an existing drill-rig without modification. Further, the apparatus 10 can be placed in multiple orientations without impeding or otherwise adversely affecting drilling activities.

The apparatus 10 is independent of the drill collar/casing 11 in the sense that it is not integrated with the drill collar/casing, and therefore offers flexibility to accommodate varying drill casing sizes and angles.

The apparatus 10 may capture all of the drilling fluid returns, and may minimise abrupt flow-diversion and/or flow velocity change which could result in particulate material falling out of suspension. Further, the apparatus 10 may prevent significant stratification of fluid flow, minimise the pooling of fluids/cuttings so as to allow efficient and near complete transfer of this material to the separation system at which at least some of the drilling cuttings are removed for sampling. The apparatus 10 may be able to maintain a flow-regime necessary to maintain predicated particles sizes in suspension. Further, the apparatus 10 may accommodate changes in flow rates, and may also allow measurement of the flow rate of captured drilling fluid returns being pumped from the sump portion 27.

It should be appreciated that the scope of the invention is not limited to the scope of the embodiment described as an example.

While the present invention has been described in terms of a preferred embodiment in order to facilitate better understanding of the invention, it should be appreciated that various modifications can be made without departing from the principles of the invention. Therefore, the invention should be understood to include all such modifications within its scope.

This disclosure is intended to explain how to fashion and use the embodiment in accordance with the technology rather than to limit the true, intended, and fair scope and spirit thereof. The foregoing description is not intended to be exhaustive or to be limited to the precise forms disclosed. Modifications or variations are possible in light of the above teachings. The embodiment was chosen and described to provide the best illustration of the principle of the described technology and its practical application, and to enable one of ordinary skill in the art to utilise the technology in various embodiments and with various modifications as are suited to the particular use contemplated.

Reference to positional descriptions, such as "upper", "lower", "top", and "bottom", "front", "rear" and "side" are to be taken in context of the embodiments depicted in the drawings, and are not to be taken as limiting the invention to the literal interpretation of the term but rather as would be understood by the skilled addressee.

Additionally, where the terms "system", "device" and "apparatus" are used in the context of the invention, they are to be understood as including reference to any group of functionally related or interacting, interrelated, interdependent or associated components or elements that may be located in proximity to, separate from, integrated with, or discrete from, each other.

Throughout this specification, unless the context requires otherwise, the word "comprise" or variations such as "comprises" or "comprising", will be understood to imply the inclusion of a stated integer or group of integers but not the exclusion of any other integer or group of integers.

The invention claimed is:

1. An apparatus for capturing drilling fluid returns from a drill collar/casing for representative sampling and/or processing of the drilling fluid returns, the apparatus comprising:
   a body having a collecting portion and a sump portion,
      the collecting portion defining a reservoir for receiving drilling fluid returns, the collecting portion being adapted for sealing engagement about the drill collar/casing so that the reservoir forms a moat around the drill collar/casing; and
      the sump portion being disposed at an angle substantially below and to a side of the collecting portion via a sloping bottom portion of the body, so that collected drilling fluid returns are able to continuously flow down from the collecting portion to the sump portion within the body to maintain particulate material therein in suspension; and
   a resilient sealing collar provided in a bottom of the collecting portion, wherein the sealing collar enables accommodation of multiple angular orientations of the drill collar/casing with respect to the body according to drilling requirements.

2. The apparatus according to claim 1, wherein the reservoir has an open top through which the drilling fluid returns flow into the reservoir, the drilling fluid returns being visible within the reservoir through the open top.

3. The apparatus according to claim 1, wherein the reservoir is configured to direct the drilling fluid returns received by the sump portion to an outlet from the sump portion.

4. The apparatus according to claim 1 wherein the resilient sealing collar comprises a frusto-conical configuration having a smaller end section configured for sealing engagement with the drill collar/casing and a larger end section in sealing engagement with the body.

5. The apparatus according to claim 1 further comprising a sump pump for pumping captured drilling fluid returns from the sump portion.

6. The apparatus of claim 5, wherein the sump pump is recessed in a bottom portion of the sump portion.

7. The apparatus of claim 1, wherein the sump portion is arranged such that the collected drilling fluid returns continuously flow down to a ground surface on which the apparatus rests, in use.

8. The apparatus of claim 1, wherein the collecting portion includes a stand to further accommodate an angular disposition of the collecting portion drill collar/casing with respect to the sump portion body.

9. The apparatus of claim 1, further comprising a side wall upstanding from the bottom portion, the side wall comprising two straight wall sections in generally opposed relation and two curved wall sections at opposed ends of the straight wall sections, with the collecting portion being defined by the two straight wall sections and one curved wall section, and the sump portion being defined by the other curved wall section.

10. The apparatus of claim 9, wherein the two straight wall sections are disposed angularly with respect to each other, wherein a spacing between the straight wall sections is larger at one of the opposed ends than at the other, and the curved wall section being at the large of the opposed ends collecting portion is defined at the end having the larger spacing.

* * * * *

UNITED STATES PATENT AND TRADEMARK OFFICE
CERTIFICATE OF CORRECTION

PATENT NO. : 10,677,003 B2
APPLICATION NO. : 15/752789
DATED : June 9, 2020
INVENTOR(S) : Fred Blaine, Andrew Beach and James Barry Reilly It is certified that error appears in the above-identified patent and that said Letters Patent is hereby corrected as shown below:

In the Claims

Claim 8, Column 10, Line 7, delete "collecting portion"

Claim 8, Column 10, Line 8, delete "sump portion"

Claim 10, Column 10, Line 21, delete "curved wall section being at the large of the opposed ends"

Signed and Sealed this
Twenty-eighth Day of July, 2020

Andrei Iancu
*Director of the United States Patent and Trademark Office*